(12) United States Patent
Playford

(10) Patent No.: US 7,426,440 B2
(45) Date of Patent: Sep. 16, 2008

(54) REPAIR AND PROTECTION FACTOR SCORING METHOD FOR BIOACTIVE AGENTS

(75) Inventor: Raymond J. Playford, London (GB)

(73) Assignee: Nutritional Bioscience Ltd., London (GB)

(*) Notice: Subject to any disclaimer, the term of this patent is extended or adjusted under 35 U.S.C. 154(b) by 402 days.

(21) Appl. No.: 10/948,924

(22) Filed: Sep. 24, 2004

(65) Prior Publication Data
US 2006/0069513 A1 Mar. 30, 2006

(51) Int. Cl.
G01N 33/48 (2006.01)
G06F 19/00 (2006.01)

(52) U.S. Cl. .................. 702/19; 703/2; 435/325; 435/385; 436/63

(58) Field of Classification Search ............ None
See application file for complete search history.

(56) References Cited

U.S. PATENT DOCUMENTS

| | | |
|---|---|---|
| 3,706,769 A | 12/1972 | Rosen et al. |
| 3,708,577 A | 1/1973 | Berger |
| 3,790,669 A | 2/1974 | Gale |
| 3,839,587 A | 10/1974 | Hoffmann et al. |
| 3,956,521 A | 5/1976 | Pisecky et al. |
| 4,141,970 A | 2/1979 | Chidlow et al. |
| 4,281,024 A | 7/1981 | Hauberg et al. |
| 4,342,747 A | 8/1982 | Liotet et al. |
| 4,440,860 A | 4/1984 | Klagsbrun |
| 4,977,137 A | 12/1990 | Nichols et al. |
| 5,130,305 A | 7/1992 | Palepu et al. |
| 5,143,727 A | 9/1992 | Ebina |
| 5,143,848 A | 9/1992 | Scholten et al. |
| 5,258,178 A | 11/1993 | Cordle et al. |
| 5,500,229 A | 3/1996 | Aalto et al. |
| 5,534,493 A | 7/1996 | Gluckman et al. |
| 5,681,586 A | 10/1997 | Gordon |
| 5,710,127 A | 1/1998 | Gluckman et al. |

(Continued)

FOREIGN PATENT DOCUMENTS

EP 0 295 009 A2 12/1988

(Continued)

OTHER PUBLICATIONS

McKaig et al., "Normal human colonic subepithelial myofibroblasts enhance epithelial migration (restitution) via TGF-beta3", 1999, American Journal of Physiology Gastrointestine Liver Physiology, vol. 276, pp. 1087-1093.*

(Continued)

*Primary Examiner*—Carolyn Smith

(57) ABSTRACT

A method of scoring the biological activity of bioactive agents like colostrum comprising conducting separate bioassays for cell restitution and cell proliferation on the bioactive agent, a comparative growth factor stimulating agent, and (preferably) a negative baseline control sample containing the cells and growth medium alone. These values are then plugged into the equations provided in this application to calculate a Restitution Score ("RS"), Proliferation Score ("PS"), and a composite repair and protection factor score ("RPF"). In this manner, the bioactivity of compositions that enhance the repair and/or proliferation of mammalian cells, or act as additives to growth media used to maintain and grow laboratory cell cultures can be quickly and reproducibly obtained. This invention may be applied to a wide variety of bioactive agents used to treat a large assortment of functional cells in organ tissues.

29 Claims, 9 Drawing Sheets

U.S. PATENT DOCUMENTS

| | | | |
|---|---|---|---|
| 6,258,383 | B1 | 7/2001 | Gohlke et al. |
| 6,277,813 | B1 | 8/2001 | Kelly |
| 6,379,676 | B2 | 4/2002 | Richardson |
| 6,475,511 | B2 | 11/2002 | Gohlke et al. |
| 6,521,591 | B1 | 2/2003 | Smeets et al. |
| 6,645,472 | B1 | 11/2003 | Anderson |
| 6,645,510 | B1 | 11/2003 | Coury et al. |
| 2001/0009681 | A1 | 7/2001 | Gohlke et al. |
| 2001/0048948 | A1 | 12/2001 | Crum et al. |
| 2002/0012722 | A1 | 1/2002 | Prosise et al. |
| 2002/0187200 | A1 | 12/2002 | Gohlke et al. |
| 2003/0003059 | A1 | 1/2003 | Dana |
| 2003/0008016 | A1 | 1/2003 | Crum et al. |
| 2003/0068391 | A1 | 4/2003 | Harris et al. |
| 2003/0198688 | A1 | 10/2003 | Cockrum |

FOREIGN PATENT DOCUMENTS

| | | |
|---|---|---|
| EP | 0 331 755 A1 | 9/1989 |
| EP | 0 338 229 A1 | 10/1989 |
| EP | 0 936 917 B1 | 11/2003 |
| EP | 0 927 042 B1 | 2/2004 |
| FR | 2 811 204 A1 | 1/2002 |
| WO | WO 98/11904 | 3/1998 |
| WO | WO 2004/041004 A1 | 5/2004 |
| WO | WO 2006/019960 A1 | 2/2006 |

OTHER PUBLICATIONS

Kelly, G., "Bovine colostrums: A review of clinical uses," *Alternative Medicine Review*, vol. 8, No. 4, pp. 378-394 (2003).

The terms "Extract", "Bioactive", and "derivative" *Merriam-Webster Online Dictionary*, http//www.m-w.com, 3 pages (Date Printed Nov. 4, 2005).

FitzGerald, A. et al., "Synergistic effects of systemic trefoil factor family I (TFF1) peptide and epidermal growth factor in a rat model of colitis," *Peptides*, vol. 25, pp. 793-801 (2004).

Marchbank, T. et al., "Dimerization of human pS2 (TFF1) plays a key role in its protective/healing effects," *Journal of Pathology*, vol. 185, pp. 153-158 (1998).

White, S. et al., "Role of Very Late Adhesion Integrins in Mediating Repair of Human Airway Epithelial Cell Monolayers after Mechanical Injury," *American Journal of Respiratory Cell and Molecular Biology*, vol. 20, pp. 787-796 (1999).

Playford, R. et al., "Colostrum and milk-derived peptide growth factors for the treatment of gastrointestinal disorders," *Am. J. Clin. Nutr.*, vol. 72, pp. 5-14 (2000).

Talley, N., "Pharmacologic Therapy for the Irritable Bowel Syndrome," *Am. J. Gastroenterol*, vol. 98, No. 4, pp. 750-758 (Apr. 2003).

Abe, M., et al., "Glycyrrhizin Enhances Interleukin-10 Production by Liver Dendritic Cells in Mice With Hepatitis," *Journal of Gastroenterology* 38(10): 962-67 (2003).

Armanini, D., et al., "Effect of Licorice on the Reduction of Body Fat Mass in Healthy Subjects," *Journal of Endocrinol. Invest.* 26: 646-50 (Jul. 2003).

Bardhan, K.D., et al., "Clinical Trial of Deglycyrrhizinized Liquorice in Gastric Ulcer," *Gut* 19: 779-82 (Sep. 1978).

Borrelli, F. and Izzo, A.A., "The Plant Kingdom As a Source of Anti-Ulcer Remedies," *Phytotherapy Research* 14: 581-91 (2000).

Chadwick, B., et al., "Hexetidine Mouthrinse in the Management of Minor Apthous Ulceration, and as an Adjunct to Oral Hygiene," *British Dent. J.*, 171: 83-7 (1991).

Chen, A.C. and Donovan, S.M., "Genistein at a Concentration Present in Soy Infant Formula Inhibits Caco-2BBe Cell Proliferation By Causing G2/M Cell Arrest," American Society for Nutritional Sciences Manuscript No. 0022-3166/04 (2004).

"Colostrum and IBS" *Gut Reaction, The Journal of the IBS Network*, Issue 50, Jul. 2003 http://www.colostrum-uk.com/news/article.asp?articleid=94.

"Colostrum" http://www.crohns.net/Miva/education/colostrum.shtml (Jul. 1, 2004).

U.S. Appl. No. 10/892,939, "Colostrum-Based Treatment for Irritable Bowel Syndrome," filed Jul. 16, 2004.

U.S. Appl. No. 10/953,244, "Improved Bioactive Agent Compositions For Repair of Cell Injuries," filed Sep. 29, 2004.

Daniel et al. "Effect of Casein and Beta-Casomorphins on Gastrointestinal Motility in Rats," *J Nutr.* 120(3): 252-57 (1990).

Dignass, A., Devaney, K.L., Kindon, H. et al., "Trefoil Peptides Promote Epithelial Migration Through a Transforming Growth Factor Beta Independent Pathway," *J. Clin. Invest.* 376-83 (1994).

Dunlop, et al. "Randomized, Double Blind, Placebo-Controlled Trial of Prednisolone in Post-Infectious Irritable Bowel Syndrome," *Aliment Pharmacol Ther* 18: 77-84 (2003).

"Feedback on Neovite and Digestive Health," http://www.colostrum-uk.com/news/article.asp?articleid=82 (Jul. 1, 2004).

Franco, L., et al., "Anti-Ulcer Activity of Carbenoxolone and ISF 3401 on PGE2 Release in Rat Gastric Mucosa," *Pharmacological Research* 27(2): 141-50 (Feb.-Mar. 1993.

Fung, W.P., "Effect of Soya Bean Milk on the Healing of Gastric Ulcers—A Controlled Endoscopic Study," *Med. J. Aust.* 1(23): 717-18 (1975).

Funk. M.A. and Baker, D.H., "Effect of Soy Products on Methotrexate Toxcity in Rats," *Journal of Nutrition* 121(10): 1684-92 (Oct. 1991).

Ghosh, S. and Playford, R.J., "Bioactive Natural Compounds for the Treatment of Gastrointestinal Disorders", *Clinical Science* 104, 547-56 (2003).

Gordon, S.R. and Wood, M., "Soybean (Glycine Max) Agglutinin Binds to Corneal Endothelial Cells During Wound Repair and Alters Their Microfilament Pattern," *Cell Molecular Biology* 43(3): 329-36 (May 1997).

"Irritable Bowel and IBD," http://www.evenbetternow.com/irritable-bowel-syndrome.html (Jul. 1, 2004).

Jones, et al. "British Society of Gastroenterology Guidelines for the Management of the Irritable Bowel Syndrome," *Gut* (Suppl II) 47: ii1-ii19 (2000).

Khan, Z., et al., "Use of the Nutriceutical, Bovine Colostrum, for the Treatment of Distal Colitis: Results from an Initial Study," *Ailment Pharmacological Therapy* 16: 1917-22 (2002).

Li, Z; et al., "Effects of Soybean Agglutinin on Nitrogen Metabolism and on Characteristics of Intestinal Tissues and Pancreas in Rats," *Arch. Tierernahr.* 57(5): 369-80 (Oct. 2003).

Madisch, A., et al., "A Plant Extract and Its Modified Preparation in Functional Dyspepsia," *Z. Gastroenterology* 39: 511-17 (Jul. 2001).

Meiller, T.F., et al.,"Effect of an Antimicrobial Mouthrinse on Recurrent Apthous Ulcerations," *Oral. Surg.Oral. Med. Oral. Pathol.* 72: 425-29 (1991).

Morales de Leon, J., et al., "Development of an Infant Food Product Based on Fermented Milk, Cereals, and Soybeans," *Arch. Latinoam Nutr.* 38(4): 852-64 (Dec. 1988).

Nokhodchi, A., et al., "The Effect of Glycyrrhizin on the Release Rate and Skin Penetration of Diclofenac Sodium From Topical Formulations," *Pharmacology* 57: 883-88 (Nov. 2002).

Olukoga, A. and Donaldson, D., "Liquorice and Its Health Problems," *Journal R. Soc. Health* 120(2): 83-9 (Jun. 2000).

Playford, R.J., et al., "Bovine Colostrum Is a Health Food Supplement Which Prevents NSAID-Induced Gut Damage," *Gut* 44:653-53 (May 1999).

Playford, R.J., et al., "Co-Administration of Health Food Supplement, Bovine Colostrum, Reduces the Acute Non-Steroidal Anti-Inflammatory Drug-Induced Increase in Intestinal Permeablility," *Clinical Science* 100: 627-33 (2001).

Playford, R.J., et al., "Effect of Luminal Growth Factor Preservation On Intestinal Growth," *Lancet* 341 (8849) (Apr. 1993).

Playford, R.J., et al., "Human Spasmolytic Polypeptide Is A Cytoprotective Agent That Stimulates Cell Migration," *Gastroenterology* 108: 108-16 (1995).

Quigley, J.D. 3rd, et al., "Addition of Soybean Trypsin Inhibitor to Bovine Colostrum: Effects on Serum Immunoglobulin Concentrations in Jersey Calves," *Journal Dairy Science* 78: 886-92 (Apr. 1995).

Rainsford, K.D., "Electronmicroscopic Observations on the Effects of Orally administered Aspirin and Aspirin-Bicarbonate Mixtures on the Development of Gastric Mucosal Damage in the Rat," *Gut* 16: 514-27 (Jul. 1975).

Rodriguez, et al. "Increased Rick of Irritable Bowel Syndrome after Bacterial Gastroenteritis: Cohort Study," *B.M.J.* 318: 565-66 (1999).

Sasaki, H., et al. "Effect of Glycyrrhizin, An Active Component of Licorice Roots, On HIV Replication in Cultures or Periphereal Blood Mononuclear Cells from HIT-Seropositive Patients," *Pathobiology* 70(4): 229-36 (2002-2003).

Shah, Nagendra P. "Effects of Milk-Derived Bioactives: An Overview," *British Journal of Nutrition* 84 Suppl. 1, S3-S10 (2000).

Stead, R.H., "Nerve Remodeling During Intestinal Inflammation," *Ann N.Y. Acad. Sci.* 664: 443-55 (1992).

Takahashi, T., et al., "Isoliquiritigenin, a Flavonoid From Licorice, Reduces Prostaglandin E2 and Nitric Oxide, Causes Apoptosis, and Suppresses Aberrant Crypt Foci Development," *Cancer Science* 95: 448-53 (May 2004).

Tanaka, H. et al., Histamine-Induced Villous Damage in the Rat Duodenum, *Japanese J. Pharmacol.* 51(2): 297-97 (Oct. 1989).

Tornblom, et al. "Full-Thickness Biopsy of the Jejunum Reveals Inflammation and Enteric Neuropathy in Irritable Bowel Syndrome," *Gastroenterology* 123: 1972-79 (2002).

Wang, W. and Higuchi, C.M., "Dietary Soy Protein is Associated With Reduced Intestinal Mucosal Polyamine Concentration in Male Wistar Rats," American Society for Nutritional Sciences, *J. Nutr.* 130(7):1815-20 (Jul. 2000).

Wang, W., et al., "Individual and Combinatory Effects of Soy Isoflavones on the Invitro Potentiation of Lymphocyte Activation," *Nutr. Cancer.* 29(1): 29-34 (1997).

Wang, Z.Y. and Nixon, D.W., "Licorice and Cancer," *Nutr. Cancer.* 39: 1-11 (Jan. 2001).

\* cited by examiner

Normal gastric epithelium

Mitosis

Damaged gastric epithelium denuded area

1 hour following damage cell migration

24 - 48 hours following damage proliferation

Remodeling

Time - 0 hrs   Time - 24 hrs

Wounded HT-29 Monolayer

Fig. 3b
Fig. 3d
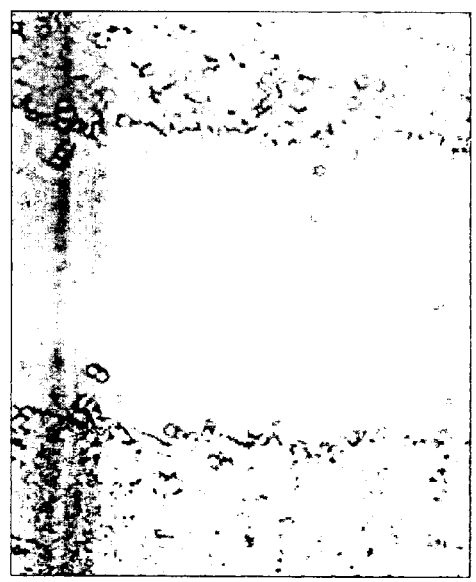
Fig. 3a
Fig. 3c

REPAIR AND PROTECTION FACTOR SCORING METHOD FOR BIOACTIVE AGENTS

FIELD OF INVENTION

This invention relates to bioactive agents used for treating cellular injuries to mammals, and as additives to growth media employed to maintain and grow laboratory cell cultures. In particular, the invention provides a reproducible and comparative method for quantitatively evaluating the bioactivity of such agents.

BACKGROUND OF THE INVENTION

Organs in humans and animals are composed of tissues, which in turn are composed of cells. Epithelial tissue covers body surfaces and lines body cavities. Endothelial cells perform a similar role in forming a lining layer in tissues, such as blood vessels, lymph tissues, and urogenital system. Connective tissue cells maintain cohesiveness between cells, and act as a "scaffold" in both normal tissues and as part of the repair cell process. Inflammatory cells, such as lymphocytes, macrophages, and neutrophils, are part of the normal repair process as well as removers of infectious agents. Epithelial, endothelial, connective tissue, and inflammatory cells are therefore important for the defense, normal structure, and repair of mammalian animals, including protecting the internal environment of the body against the external environment, and containing fluids in various organs.

Such organs of the human or animal body include the gastrointestinal system, which in turn includes the stomach and the small and large intestines. Eaten food is collected in the stomach, whereupon it is digested in the duodenum portion of the small intestines, and then passed on to the jejunum and ileum portion of the small intestines where the nutrients (e.g., fatty acids, sugars, amino acids) from the digested food are absorbed. The remaining digesta is then passed along to the large intestine (sometimes called the "bowel" or "gut") in which fluids from this solid mass of digested food are absorbed. The leftover, used portion of the food enters the rectum for subsequent discharge from the body.

The epithelial tissue lining of the gastrointestinal tract possess the remarkable ability to remain intact despite being constantly bathed in acid and proteolytic enzymes that can digest virtually any form of food that is eaten. When a superficial mucosal injury occurs, such as following direct physical trauma or ingestion of noxious agents like aspirin or alcohol, it is rapidly healed. This healing process is achieved through migration of surviving cells around the wound edge to cover the denuded area of the tissue within the first hour after the injury, followed by differentiation and multiplication ("proliferation") of the cells beginning one to two days after the injury. Finally, remodeling occurs where the mucosa slowly re-establishes an essentially normal looking mucosa. The intestines therefore possess powerful mucosal defense and repair mechanisms.

In general, an ulcer is any eroded area of the skin or mucous membrane marked by tissue disintegration. More commonly, however, ulcer is used to refer to disorders in the upper digestive tract. It is estimated that approximately 10% of the United States population will develop an ulcer at some point in their lives. Peptic ulcers can develop in the lower part of the esophagus, the stomach, and the duodenum and jejunum portions of the small intestines. Peptic ulcers are caused by infection by *Helicobacter Pylori* bacteria; nonsteroidal anti-inflammatory drugs (NSAIDs) like aspirin, ibuprofen, flurbiprofen, ketoprofen, and indomethacin; and disorders like Zollinger-Ellison syndrome that cause over-secretion of stomach juices. Symptoms for such peptic ulcers include heartburn, stomach pain relieved by eating or antacids, weight gain, and a burning sensation at the back of the throat.

Gastric ulcers account for about 16% of peptic ulcers, and are most commonly caused by the use of NSAIDs, or by *Helicobacter* infection. Symptoms of gastric ulcers include feelings of indigestion and heartburn, weight loss, and repeated episodes of gastrointestinal bleeding.

About 5% of ulcer patients actually develop perforations, which are holes in the duodenal or gastric wall through which the stomach contents can leak out into the abdominal cavity. Emergency surgery may be required to treat such a perforation.

Fortunately, however, most peptic and gastric ulcers can be medicated with drugs to create chemical reactions that either lower the rate of stomach acid secretion, or protect the mucous tissues that line the digestive tract. Such antisecretory drugs include: proton pump inhibitors, which bind an enzyme that secretes stomach acid, like omeprazole (Prilosec) and lansoprazole (Prevacid); or $H_2$ receptor antagonists like ranitidine (Zantac), cimetidine (Tagamet), famotidine (Pepcid), or nizatidine (Axid). Drugs currently used to protect the stomach tissues include sucralfate (Carafate), bismuth preparations, and misoprostol (Cytotec). These drugs act to neutralize disorders like excessive acid secretion that would otherwise interfere with the natural function of cell migration and proliferation to heal the ulcer.

It has been found, however, that alternative treatments using bioactive agents instead of traditional drug chemicals can effectively treat ulcers by rebalancing the stomach's hydrochloric acid output, and/or enhancing the mucosal lining of the stomach and intestines through promotion of these natural cell migration and proliferation functions. Such bioactive agents include plant extracts like aloe vera, deglycrrhizinated licorice (DGL) in a chewable or powder form, raw cabbage juice, substances of animal origin, artificially produced nutritional molecules like zinc-carnisine, and artificially made normal proteins like recombinant human spasmolytic polypeptide (hSP). One particularly important example of an animal-originated bioactive agent is colostrum, which is the first milk produced after birth, and has been shown to enhance the cell migration and growth healing function of ulcerated digestive tracts caused by NSAIDs. See Playford, R. J., Floyd, D. N., MacDonald, C. E. et al., "Bovine Colostrum in a Health Food Supplement Which Prevents NSAID—Induced Gut Damage," *Gut* 44: 653-58 (1999); Playford, R. J., MacDonald, C. E., Calnan, D. P. et al., "Colostrum, Reduces the Acute, Non-Steroidal, Anti-Inflammatory Drug-Induced Increase In Intestinal Permeability," *Clinical Science* 100: 627-33 (2001). Similarly, another study has shown that hSP may be used to enhance cell migration in order to reduce gastric damage by 50%. See Playford, R. J., Marchblank, T., Chinery, R. et al., "Human Spasmolytic Polypeptide Is A Cytoprotective Agent That Stimulates Cell Migration," *Gastroenterology* 108: 108-16 (1995). Zinc-Carnisine manufactured by Lonza Inc. of Allendale, N.J. may also be used to treat stomach ulcers and gastric reflux.

Ghosh, S. and Playford, R. J., "Bioactive Natural Compounds for the Treatment of Gastrointestinal Disorders", *Clinical Science* 104, 547-56 (2003), provides a survey of many other bioactive compounds that have been found useful for the treatment of various gastrointestinal disorders. For example, curcumin capsules improve endoscopic healing of peptic ulcers, as well as improving symptoms of patients with non-ulcer dyspepsia. *Sangre de grado* has also been shown to heal experimental gastric ulcers induced by application of 80% acetic acids in rats. Moreover, acemannan, a component of aloe vera, prevents stress-induced gastric ulceration in rats.

Other organs within the human or animal body share the same natural cell migration, proliferation, inflammation, and other healing functions for addressing an injury to the epithelial, endothelial, or connective tissue, and which can also be influenced directly or indirectly by bioactive products. For example, mouse ear or rat hind paw inflamed by the application of croton oil was helped by the topical application of aloe gel. Similarly, topical honey has been shown to be effective in treating postoperative skin wounds in neonates that had failed to respond to antibiotic therapy. Acemannan has been reported to accelerate healing and reduce pain in aphthous stomatitis. Milk whey has exhibited beneficial effects for patients with chemical-induced corrosive injuries. Corneal abrasions of the eye may be treated with bioactive agents like epidermal growth factor (EGF) or hSP. If these bioactive products are to be used effectively to influence such processes in a reliable manner, then it is important that consistency and accuracy in quality control is provided. Bioactive products, particularly mixed protein constituents like bovine calf serum, are vital additives for the long-term maintenance of mammalian cells grown in laboratory cultures, e.g., for production of antibodies. Reduction of the variation in biological activity of these additives is therefore highly desirable for allowing stability of these cells over time.

Currently, manufacturers measure amounts of constituents such as levels of total protein or immunoglobulins in colostrum or total amount of chemical constituents in other products as a crude indicator of their predicted effectiveness. Unfortunately, this approach for measuring the bioeffectiveness of the active ingredients in these bioactive agents has a number of shortcomings. For example, it disregards the fact that biological activity in a composition may decrease over time due to factors like oxidation or degradation of proteins. Thus, the same sample of a bioactive agent may exhibit different levels of enhancement of cell migration or cell proliferation function between two different days. Likewise, two different preparations of the same type of the bioactive agent may exhibit differing levels of cell migration or cell proliferation enhancement when tested the same day. Moreover, for many neutraceuticals, the factors that are causing the biological activity are incompletely understood or identified, so a characteristic like total protein may turn out to be irrelevant to the composition's biological activity.

Being able to accurately characterize biological activity therefore would be very advantageous to both manufacturers and end users by showing that a commercial product is truly active, and that a standardized product is being manufactured. Furthermore, a characterization method for biological activity that is reproducible and permits comparison of different lots of the same bioactive agent or different bioactive agents altogether would provide a great benefit.

SUMMARY OF THE INVENTION

A method of scoring the biological activity of bioactive agents like colostrum is provided according to the invention. Separate bioassays for cell restitution and cell proliferation are conducted on the bioactive agent, a comparative growth factor stimulating agent, and (preferably) a negative baseline control sample containing the cells and growth medium alone. These values are then plugged into the equations provided in this application to calculate a Restitution Score ("RS"), Proliferation Score ("PS"), and a composite "Repair and Protection Factor Score." In this manner, the bioactivity of compositions that enhance the repair and/or proliferation of mammalian cells, or act as additives to growth media used to maintain and grow laboratory cell cultures can be quickly and reproducibly obtained. This invention may be applied to a wide variety of bioactive agents used to treat a large assortment of functional cells in organ tissues.

BRIEF DESCRIPTION OF THE DRAWINGS

In the accompanying drawings:

FIG. 3 is photographs showing the effect of colostrum on cell restitution, compared with a negative baseline control.

DETAILED DESCRIPTION OF THE EMBODIMENTS

Figure 1A:
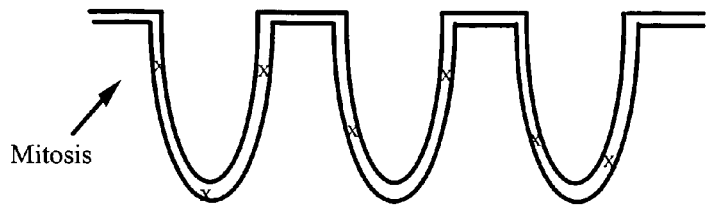
FIG. 1 is a series of schematic drawings showing normal and damaged epithelial, endothelial, or connective tissue, along with representations of the natural restitution, proliferation, and remodeling processes for healing such damaged tissue.
Figure 1B:
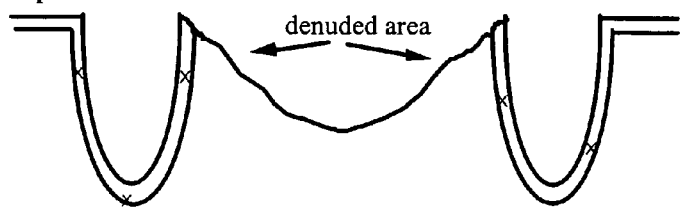

Use of a scoring method for assessing the bioactivity of compositions that enhance the repair and/or protection of epithelial, endothelial, connective, or inflammatory tissue cells and tissue containing such cells is provided by the invention. Such as a scoring method may also be used to assess the bioactivity of compounds employed as additives to growth media used to maintain and grow laboratory cell cultures. In particular, the invention facilitates quality control measures for reproducible production of such bioactive compositions.

FIG. 1 shows the three phases of the healing process when an injury occurs to epithelial, endothelial, or connective tissue cells. For example, the normal gastric epithelium is represented in FIG. 1a. On the other hand, an injury is represented by the denuded region of the gastric epithelium shown in FIG. 1b. Within 1 hour after the injury, a rapid response will typically occur, involving migration of surviving cells from the wound edge to cover the denuded area, as shown in FIG. 1c. This step is termed "restitution." One to two days after the injury has occurred, a much slower increase in the number and differentiation of cells takes place to finish filling the damaged region of the gastric epithelium (FIG. 1d). This second stage is called "proliferation." The final stage of the healing process is "remodeling" (FIG. 1e) in which the mucosa slowly reestablishes an essentially normal looking mucosa along the surface of the gastric epithelium.

For purposes of the present invention, "functional cells" means any cells relevant to the defense, normal structure, or repair of mammalian animals, including epithelial, endothelial, connective tissue, and inflammatory cells. HT-29 and keratinocytes are examples of epithelial cells. Mouse pancreatic islet endothelial cells (MS1) and human endothelial cells derived from the umbilical vein are examples of endothelial cells. Connective tissue cells include fibroblasts and vascular smooth muscle cells. Neutrophils, plasma cells, lymphocytes, and dendritic cells are examples of inflammatory cells.

In the context of the present invention, "organ tissue" means any organ of the human or animal body characterized by having functional cells. This includes the stomach, small intestines, large intestine, skin, corneum portion of the eyes, vagina, bladder and urogential system, pancreas, spleen, thymas, respiratory tract, and blood vessels including the heart.

For purposes of the present invention, "bioactive agent" means any natural or manufactured substance that is effective for enhancing the restitution and/or proliferation of cells, or of influencing the immune function of cells in organ tissue that has been damaged. The cause of such damage may include, but is not limited to, gastric ulcers, peptic ulcers, inflammatory bowel disease ("IBD"), necrotizing enterocolitis, short bowel syndrome, skin wounds, corneal abrasions, cystitis, vaginitis, mouth ulcers, atherosclerosis, and lung damage such as emphysema and chronic obstructive airways disease. Such bioactive agents may constitute natural unicellular or multicellular products plant, animal, marine, or insect origin, or derivatives from such natural products. The recently published article Gosh, S. and Playford, R. J., "Bioactive Natural Compounds for the Treatment of Gastrointestinal Disorders"*Clinical Science* 104: 547-56 (2003) discusses a number of these compounds in some detail, and is hereby incorporated by reference. Examples of such bioactive agents include:

Bacteria and Yeasts: Probiotics; botulinum toxin from the anaerobic bacteria *Clostridium botulinum*.

Plant Sources: Prebiotics like chicory root, non-digestible oligosaccharides, and low-digestable carbohydrates; symbiotics entailing products in which a prebiotic and a probiotic are combined; aloe vera and some of its individual constituents such as acemannan; soybean and its derivatives; tumeric and its individual constituents such as Curcumin; bael (Aegle marmelos); garlic, pine bark extract; dragon's blood (Sangre de grado).

Other plant derivatives include dithiolthiones, glucosinolates and isothiocyanates (cruciferous vegetables), coumarines, and limonene (citrus fruits), isoflavones inositol hexaphosphate, protease inhibitors and saponins (soybean), carotenoids (palm oil, yellow vegetables) and allium compounds (onion, garlic and leek) and prebiotics such as inulin, fructo-oligosaccharides and soybean oligosaccharides and Chicory fructo-oligosaccharides (ChiFos).

Animal Sources: Colostrum and derivatives obtained from it or artificially produced such as cytokines, including interleukin (IL)-1beta, IL-6, IL-10, TNF-alpha, and granulocyte macrophage colony stimulating factors, nucleosides and nucleotides, and a variety of other growth factors including transforming growth factor alpha and beta, insulin like growth factor 1 and 2, epidermal growth factor, and granulocyte colony stimulating factor.

Milk derived products such as caseins and their subfractions ($\alpha_{s1}$, $\alpha_{s2}$, $\beta$ and $\kappa$ caseins), whey and its subfractions $\alpha$-lactalbumin, $\beta$-lactoglobulin, lactoferrin, lactoperoxidase, immunoglobulins, glycomacropeptide and a variety of growth factors, including the EGF-receptor ligand, beta-cellulin.

Blood serum obtained from mammals like cows, pigs, goats, or rabbits.

Other animal sources such as Deer antler and velvet.

Marine Sources: Fish oils such as eicosapentaenoic and docosahexanenoic acids; proteins, amino acids and other subcomponents obtained or derived from fish origin; derivatives obtained from other marine sources (such as Sponges and snails) including manoalide, and contignasterol.

Insect Sources: Honey; royal jelly.

Other Sources: Proteins, peptides and other factors produced naturally or artificially produced from bacterial, yeast, mammalian or insect cells based on natural products such as epidermal growth factor, trefoil peptides, and pancreatic secretory trypsin inhibitor. Analysis may be performed on individual products or in combination where additive or synergistic effects may be considered. Derivatives of such products include modifying amino acid sequences to improve stability or activity, or complexing with products, such as zinc, iron, etc.

The bioactive agent can be administered to humans, as well as domesticated animals like dogs, cats, and horses, and work animals like pigs and cows.

For each of these potential sources, application may also apply to derivatives such as heat-treated sources that have undergone partial extraction using methods like alcohol extraction, and sources that have undergone partial or complete enzymatic or mechanical digestion.

Colostrum shall be used as an exemplary bioactive agent for purposes of this application and the new repair and protection factor scoring system claimed hereunder, but it is important to appreciate that the invention can be applied to any product that influences cell migration or proliferation. Colostrum is the first milk produced after birth, and is particularly rich in non-specific and specific anti-microbial factors like immunoglobulins and other bioactive molecules including non-peptide factors, such as nucleotides, and a whole variety of peptide growth factors such as epidermal growth factor ("EGF"), transforming growth factor-alpha ("TGF-$\alpha$"), insulin-like growth factors I and II, vascular endothelial growth factor, platelet-derived growth factor, and lactoferrin. In combination with the milk that is subsequently produced by the mother, colostrum is an important contributor to the nutrition, growth, development, and immunological defense of the newborn infant.

Bovine colostrum is commonly produced as a side product by the milk industry. It is currently available in health food stores, where it is usually marketed as a general health promoting agent. However, it has also been shown that bovine colostrum, growth factor enriched colostrum, or purified peptides derived from colostrum can be employed to prevent or reduce perforation of the wall of the small intestine caused by NSAIDs like asprin, ibuprofen, and indamethacin. See Playford, R. J., Floyd, D. N., MacDonald, C. E. et al., "Bovine Colostrum is a Health Food Supplement Which Prevents NSAID-Induced Gut Damage," *Gut* 44: 653-58 (1999); Playford, R. J., MacDonald, C. E., Calnan, D. P., et al., "Co-Administration of the Health Food Supplement, Bovine Colostrum, Reduces the Acute Non-Steroidal Anti-Inflammatory Drug-Induced Increase in Intestinal Permeability," *Clinical Science* 100: 627-33 (2001). See also EPO Patent Nos. 927,042 and 936,917 issued to Johnson and Playford. In another study, it has been demonstrated that patients suffering from distal colitis (a type of inflammatory bowel disease, "IBD") showed marked improvement after taking a colostrum enema in combination with oral administration of the 5-aminosalicylic acid mesalazine, compared with the control group receiving mesalazine and a placebo enema. See Khan, Z., MacDonald, C., Wicks, A. C., et al., "Use of the 'Nutriceutical', Bovine Colostrum, for the treatment of Distal Colitis: Results from an Initial Study," *Ailment Pharmacol. Ther.* 16: 1917-22 (2002). For such IBD symptoms, the growth factors contained in the colostrum stimulate the intestinal cells to repair themselves through proliferation, restitution and possibly immune modulation.

It is also likely, however, that all commercial preparations of colostrum are not equal in terms of their methods of preparation, storage conditions, and other manufacturing practices (e.g., solution or tablet form), which may markedly affect the biological activity of the colostrum preparation and bioavailability of its active ingredients. Co-pending application U.S. Ser. No. 10/892,939 filed on Jul. 16, 2004 by the inventor of the present application discusses in greater detail preparation, storage, and manufacturing methods for liquid, powder, tablet, and capsule forms of colostrum products, and its specification is incorporated by reference into the present application. Therefore, although the total amount of constituents in the colostrum composition, such as total protein or immunoglobulin levels, may be the same, there could be major differences in biological activity between colostrum products, and in the same colostrum product over time. Similarly, the biological activity present in the initial bulk colostrum product, usually purchased on a wholesale basis, may be radically altered by the subsequent differing processing methods utilized by a manufacturer or between different manufacturers.

The following examples illustrate several of these points.

EXAMPLE I

Effect of Colostrum as a Bioactive

Agent on Cell Migration

Figure 1C:
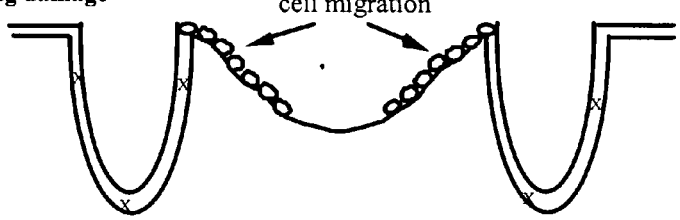

As discussed above, one of the earliest biological repair responses following injury to tissue cells is the migration of surviving cells over the denuded area caused by the injury to reestablish epithelial integrity (See FIG. 1c). Since it is extremely difficult to study this effect upon organ tissue inside a human or animal, cell culture models are commonly used as surrogate markers of this pro-migratory response. Several cell lines are potentially available for performing these studies, which include human colon cells such as HT-29 and caco2 cells, human intestinal lines like HIE cells, and rat intestinal cell lines like RIE6, gastric cell lines like AGS and other similar cell lines such as IEC -6 and IEC 17 cells, T84 and NRK cells. The generality of these results allow them to be applied to the study of cell migration responses for human applications of bioactive agents like colostrum, and for the testing of such products for animal applications.

Accordingly, the human colonic cancer cell line HT-29 was grown to confluence in six well plates in a solution of DMEM-containing glutamine and 10% fetal calf serum. The monolayers of the cells were then wounded by scraping a disposable pipette tip across the dishes, washed with fresh serum-free medium, and then cultured in a serum-free medium in the presence of 1 mg/ml, 2 mg/ml, and 5 mg/ml colostrum solutions. The rate of movement of the anterior edges of the wounded monolayer cells was then determined by taking serial photomicrographs at various times after wounding (i.e., 0, 4, 8, 12, and 24) hours, using an inverted Nikon TS100 microscope and a Nikon Coolpix 800 digital camera with 100-fold magnification. Identical regions were examined at each time point by premarking the base of the plates to facilitate alignment. Twenty measurements per field were performed by placing a transparent grid over the photomicrograph, and measuring the distance moved by the anterior edge of the cells from the original wound line. Each wound was examined in at least three different regions, and expressed as mean and SEM of three separate experiments.

Figure 2:
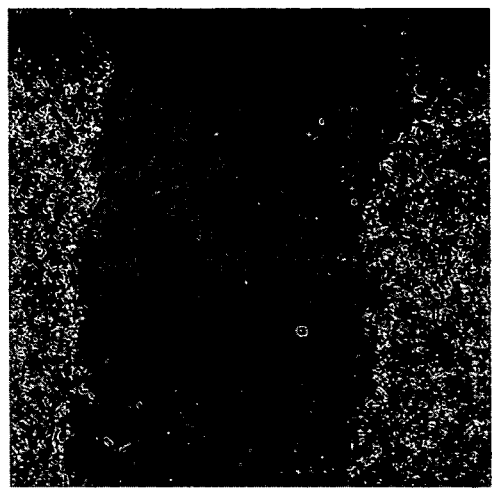
FIG. 2 is photographs showing a wounded HT-29 monolayer at times 0 and 24 hours.
Figure 2:
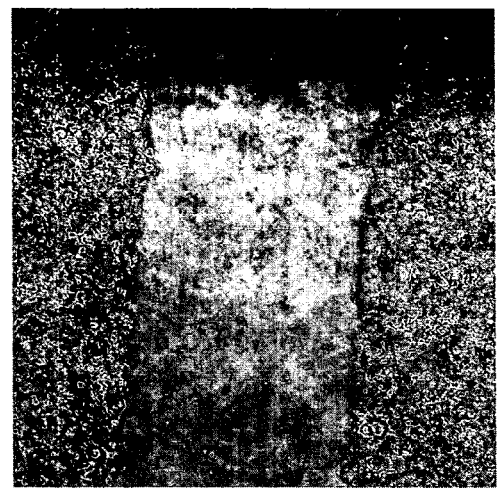

FIG. 2 compares the photomicrographs for the same wounded HT-29 cell monolayer at times t=0 and t=24 hours where no test factor was added (i.e., DMEM alone). One can easily see the natural movement of the anterior edge of the cell monolayer due to the passage of time. FIG. 3 shows pictures taken at the start of an experiment (FIGS. 3a and 3c) and eight hours later (FIGS. 3b and 3d) of cells that were grown in culture medium containing DMEM alone (FIGS. 3a and 3b) versus where commercial colostrum sourced from Sterling Technology, Inc. of Brookings, S. Dak. was added to the cell culture media at 1 mg protein/ml (FIGS. 3c and 3d). As can be clearly seen, the gap produced by wounding in the negative control (DMEM alone) well started off as roughly the same size as the gap in the well of cells to which the colostrum was added. However, eight hours later, the gap was much smaller in the wells where the colostrum was added, reflecting an increase in the rate of movement of the anterior edge of the cell monolayer, compared with the negative control well. Indeed, by 24 hours, the gap completely closed in wells where colostrum was added (not shown).

Figure 4:
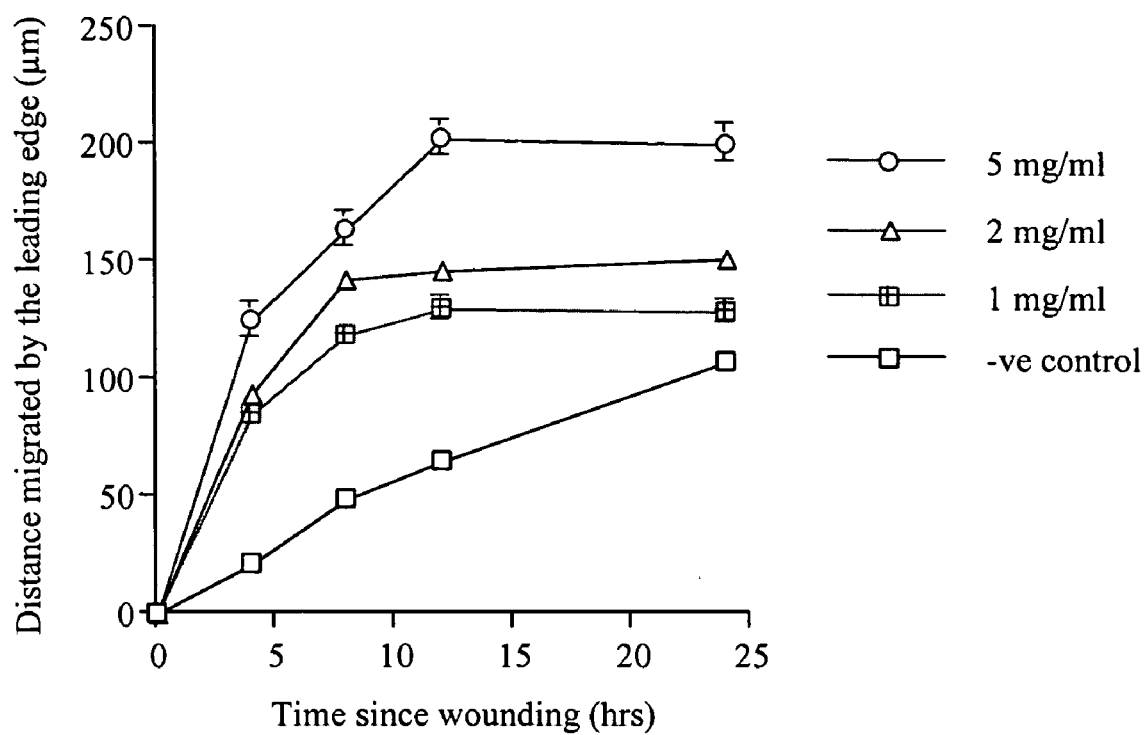
FIG. 4 is a graph comparing the effect of the same colostrum sample at different concentrations on cell restitution, compared with a negative baseline control, over time.

The dose response for the migratory distanced traveled by wounded HT-29 cell monolayers incubated with 1 mg protein/ml, 2 mg protein/ml, and 5 mg protein/ml colostrum solutions is shown in FIG. 4. While all three colostrum solutions induced enhanced cell migration compared with the control sample, at 12 hours, the 5 mg protein/ml colostrum sample produced approximately 200 μm of movement by the anterior edge of the cell monolayer, while the 1 mg protein/ml colostrum sample produced approximately 130 μm of cell movement (compared with approximately 60 μm for the control sample), thereby demonstrating that increased concentrations of colostrum appear to have induced increased amounts of cell migration.

Figure 5:
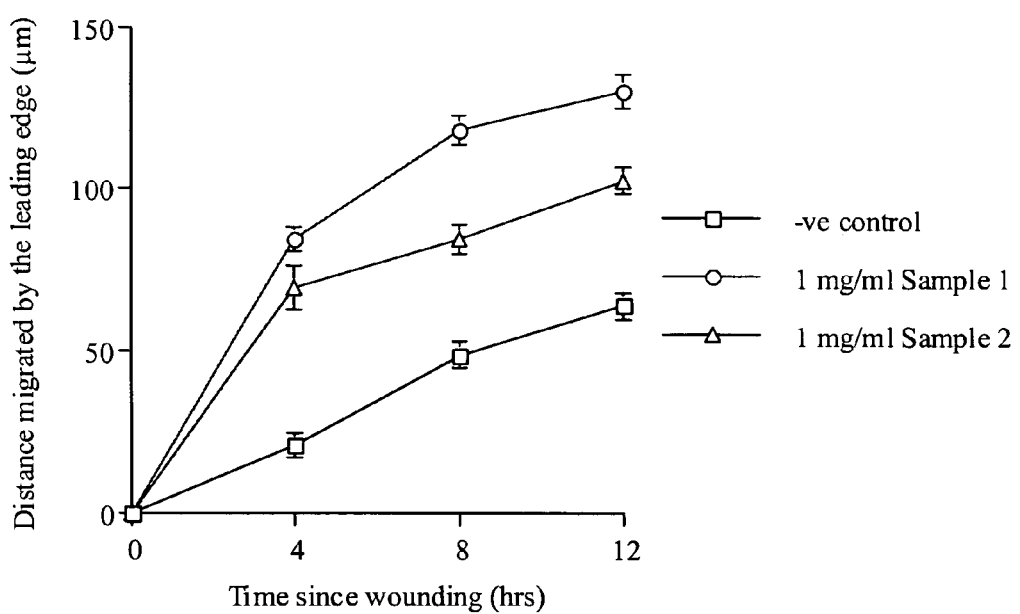
FIG. 5 is a graph comparing the effect of two different colostrum samples at the same protein concentration on cell restitution, compared with a negative baseline control, over time.

FIG. 5 shows the results of cell movement for three cell cultures incubated in DMEM alone (negative control), or in the co-precense of one of the two different colostrum products under study (Samples 1 & 2), each added at the same 1 mg protein/ml protein concentration. Once again, while both Sample 1 and Sample 2 exhibit a positive dose response on cell migration compared with the negative control sample, the differing results at t=8 hours for Sample 1 (approximately 120 μm) vs. Sample 2 (approximately 80 μm) demonstrates the misleading practice of expressing bioactive agents only in terms of protein concentration.

A further problem is that the same colostrum sample, tested using the biological assay described above at the same protein concentration, but on different days, may induce different degrees of cell migration. For example, at t=8 hours, a colostrum sample at 1 mg/ml protein may cause the anterior edge of the wounded cell cultures to move by 100 μm Day 1, but only by 75 μm on Day 2. These results are typical of the usual biological variation seen for such cell systems.

EXAMPLE II

Effect of Colostrum as a Bioactive

Agent on Cell Proliferation

Figure 1D:
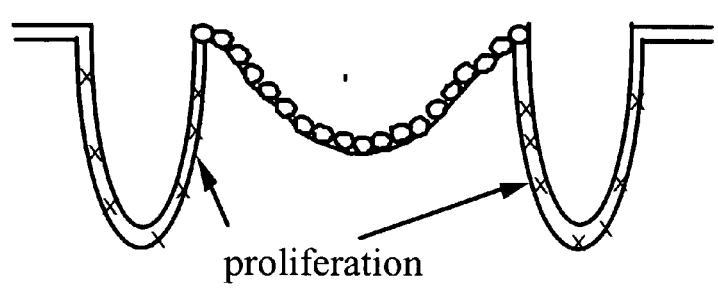
Figure 1E:
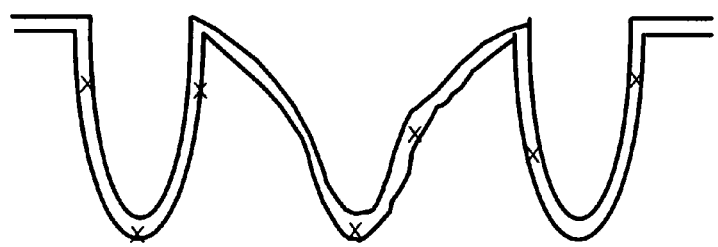

As discussed above, an increase in the rate of cell division also plays a key role in reestablishing a normal mucosa along the epithelial or endothelial tissue lining following an injury (FIG. 1d). Cell culture models have traditionally been used as surrogate markers for this proliferation response. Because thymidine is a natural constituent of the DNA within cells, thymidine incorporation is commonly used as a marker of proliferation. Cells that are actively dividing will therefore increase their uptake of thymidine in the preparatory state of cell division.

Figure 6:
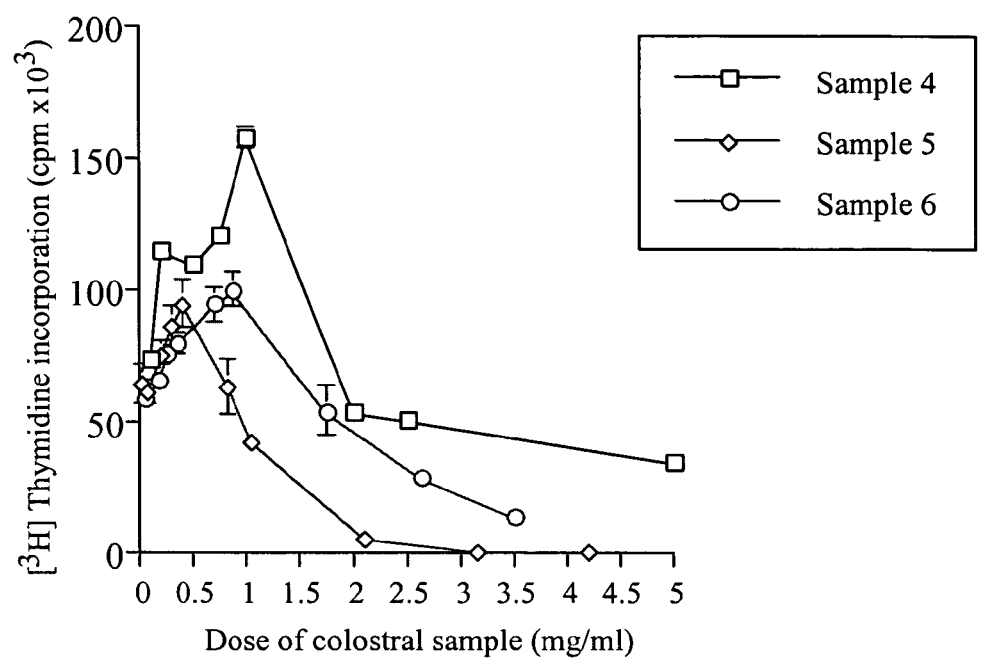
FIG. 6 is a graph comparing the effect of three different colostrum samples on cell proliferation (thymidine uptake) at different dosage levels.

FIG. 6 demonstrates the results of a typical experiment. The human colonic cancer cell line HT-29 was grown in a solution of DMEM-containing glutamine and 10% foetal calf serum. The effects of three different colostral samples, added at various concentrations, were subsequently tested under serum-starved conditions. In order to assess the percentage of cells entering DNA synthesis, [$^3$H]-thymidine (2 μCi/well) was introduced 24 hours after the addition of the different colostrum preparations, and the cells were left for a further 24-hour period. For each condition, the stimulatory or inhibitory effect of the solutions was measured in quadruplicate in six separate wells. Cell viability, determined by the ability to exclude 0.2% trypan blue, was greater than 90%.

The results are shown in FIG. 6. In wells in which no colostrum was added (i.e., the negative "baseline" control), thymidine incorporation was about 60,000 counts per minute ("CPM") (see where the lines intersect the y-axis). Wells which had differing amounts of colostrum added exhibited higher or lower amounts of thymidine incorporation, depending upon the dosage of colostrum that had been added, and, as is often seen for agents with growth factor activity, cell proliferation assays of the three different colostrum preparations revealed "bell-shaped" dose response curves. FIG. 6 shows the thymidine incorporation response stated in terms of "counts per minute" for these three different colostrum products. As can also be seen, the degree of thymidine uptake differs significantly for these three different colostrum samples even when applied at the same protein concentration. This shows that not all colostrum preparations are identical in terms of biological activity, even if added to the cell cultures at the same final protein concentration.

In a similar way to that discussed as Example 1 where cell migration was being measured, a further problem for analyzing cell proliferation is that a single sample, tested in this assay at the same concentration on different days, may cause a different peak value for thymidine uptake. For example, on Day 1, a colostrum sample added to the cell culture medium at 1 mg protein/ml protein may cause a peak incorporation rate of 150,000 cpm, while on Day 2 it might give a value of only 100,000 cpm. These differing values are due to the usual biological variation seen in such cell systems, and also the fact that tritiated thymidine has a natural radioactivity decay half life. Therefore, the freshness of the thymidine marker will influence the absolute counts obtained.

RPF Scoring Method of the Present Invention

In order to overcome the non-reproducible and non-standardized results inherent in the use of the traditional bioassays summarized in Examples I and II, the present invention provides a modified method that produces standardized scores for cell migration and cell proliferation, which, in turn, may be used to produce an overall RPF score for a bioactive agent. The method involves analyzing, in addition to the negative control wells and the wells containing the bioactive agent, a further series of wells that have been given a standard amount of a comparative growth factor stimulating agent. The cells in these wells are then grown and analyzed in an identical way and at the same time as the wells acting as the negative controls and wells in which the bioactive agent samples have been added. The effects of the bioactive agent on the amount of cell restitution and proliferation can then be accurately and reproducibly quantitated, by directly comparing the amount of proliferation or restitution seen in these wells against those found in the wells given the comparative growth factor stimulating agent using a series of simple mathematical formulae. This method may be easily employed to provide reproducible results for the same sample over time, or to enable ready comparisons of different samples of the same bioactive agent, or different bioactive agent products.

A. Cell Migration Bioassay

The shape of the curves shown for the data in FIG. 5 suggest that a single time point measurement at eight hours following wounding will provide optimal differentiation for purposes of cell migration measurement. While any time between 4 hours and 24 hours after wounding may be used for purposes of the cell migration bioassay of the invention, 8 hours is preferred.

The bioactive agent should be added to all the wells of the cell culture except for those wells that are being used as the "negative control" (which contains the cells and culture medium alone), and those wells being used as the "positive control" (which will contain culture medium, cells and a standard amount of reference growth factor such as EGF). The bioactive agent will be added at a protein concentration between 0.01-10 mg protein/ml, preferably 0.1-5 mg protein/ml, most preferably 1 mg protein/ml. Because a concentration of 1 mg protein/ml is below the maximal stimulatory response for this bioactive agent (see FIG. 4), it is preferred.

In order to standardize this cell migration bioassay, an enabling amount of a comparative growth factor stimulating agent, preferably in its fully active form should be added to separate wells containing the cell line. Note that the bioactive agent under assessment is not added to these wells. EGF is an example of such a comparative growth factor stimulating agent with the 53 amino acid-long version of human sequence EGF (EGF1-53) being preferred. Other non-EGF comparative growth factor stimulating agents are other peptides that can be used to stimulate growth and/or movement of cells. These include, but are not limited to members of the following families: hepatocyte growth factor, fibroblast growth factor family, vascular endothelial growth factor, insulin-like growth factor family, transforming growth factor-β family, platelet-derived growth factor, basic fibroblast growth factor, members of the trefoil factor family, and keratinocyte growth factor. Some of these growth factors may only influence restitution in some of the cell lines used (e.g., trefoil peptides, such as hSP, pancreatic secretory trypsin inhibitor, and transforming growth factor-β). Others may affect proliferation, but not cell movement. Comparative growth factor stimulating agents for purposes of this invention go beyond peptides to include standard amounts of factors such as the amino acid glutamine, fatty acids such as butyrate, or derivatives of natural products like zinc carnosine.

In assays of proliferation or restitution, it is sometimes necessary to check that the cells are healthy and capable of responding. Under these circumstances, a factor such as EGF is commonly added to some of the wells to show that this increases the cell movement or growth. When all the results are subsequently analyzed, if the cells containing the EGF have not responded at all, then the system is considered to be non-viable, and the test results are ignored. Note, however, that this conventional usage of EGF does not employ the EGF as a direct comparator with the test factor under analysis, as is the case for the present invention.

An "enabling amount" of the comparative growth factor stimulating agent for purposes of this invention means a sufficient dosage to stimulate restitution or movement of the cells in the system by 50-100% of that maximally achievable using that particular comparative growth factor stimulating agent, more preferably 75-100%, most preferably 100%. The absolute concentration will therefore vary according to which comparative growth factor stimulating agent is to be used, and also the cell line to which it is to be applied. Such concentration determinations are well known in the art. In the case of EGF1-53 with HT-29 cells, this concentration happens to be 10 μg/ml. If a different growth factor or cell line is used, then a different concentration may be appropriate.

While the comparative growth factor stimulating agent should preferably be used in its fully active form, some forms of the comparative growth factor stimulating agents defined above are not fully active (e.g., EGF1-48), but still can be used for purposes of this invention.

The amount of cell migration that has occurred in the cell culture wells that contain the comparative stimulating growth factor agent (positive control) should then be determined at the same time point as that applied to the cell culture wells that contain the test bioactive agent and the cell culture wells that are acting as a negative baseline control and simply contain the cells in a culture medium like DMEM, RPMI, MEM EXVIVO, or chomedia in the absence of the comparative stimulating growth factor agent or test factors. For example, taking the results summarized above in Example I, if EGF on Day 1 caused a movement of the anterior edge of the wounded cell culture of 100 μm after 8 hours, and 75 μm on Day 2, using EGF as the standard, then the same biological activity of colostrum is seen on both days with respect to what is seen for the EGF sample.

The final Restitution Score may for the colostrum sample can then be calculated using the following formula:

$$RS = \left(\frac{A-B}{C-B}\right) \times 10$$

where:

A=amount of movement of the anterior edge of the cells at the measurement time point for the wells containing the bioactive agent sample under assessment at the chosen concentration, along with the cells and culture medium.

B=amount of movement of anterior edge of the cells at the measurement time point for the negative baseline control sample (containing the cells and culture medium only).

C=amount of movement of anterior edge of the cells at the measurement time point for the positive control containing the cells, culture medium and the comparative growth factor stimulating agent sample used at the enabling concentration.

For purposes of this invention, the closer RS is to 10 the more ideal that the bioactive agent is with respect to the pure comparative growth factor stimulating agent for purposes of enhancing cell migration, although the RS score for the bioactive agent may exceed that of the comparative growth factor stimulating agent to as much as 20.

While the description of this Cell Migration Bioassay has included a correction factor B for the baseline (negative) control, it is important to note that the scoring method may omit this factor in order to provide a simpler and quicker test that will not require the culturing of as many wells. In this case, the Restitution Score would be calculated by the formula:

$$RS = \left(\frac{A}{C}\right) \times 10$$

where, as above:

A=amount of movement of anterior edge at the measurement time for the bioactive agent sample at the chosen concentration.

C=amount of movement of anterior edge at the measurement time for the positive control containing the comparative growth factor stimulating agent used at the enabling concentration.

While this method without inclusion of the baseline negative control may be simpler and quicker to perform, it will lose some of the precision incorporated into the $$RS = \left(\frac{A-B}{C-B}\right) \times 10$$

formula, because it does not correct for instability of the system. Therefore, the $$RS = \left(\frac{A-B}{C-B}\right) \times 10$$

formula is preferred for purposes of the Cell Movement Bioassay.

While the description of this Cell Migration Bioassay has used the movement of the anterior edge of the wounded monolayer as the determined factor, it is important to note that the scoring method may, as an alternative, count the actual number of cells that have crossed the initial wound line at the measurement time. This technique for counting numbers of cells is demonstrated in the publication by Dignass, A., Devaney, K. L., Kindon, H. et al., "Trefoil Peptides Promote Epithelial Migration Through a Transforming Growth Factor Beta Independent Pathway," *J. Clin. Invest.* 376-83 (1994). In the case of using the number of cells that have crossed the wound line as the determining criteria for measuring the cell migration, the Restitution Score would be calculated using the same $$RS = \left(\frac{A-B}{C-B}\right) \times 10$$

formula:

where:

A=Number of cells that have crossed the wound line at the measurement time point for the wells containing the bioactive agent sample under assessment at the chosen concentration, along with the cells and culture medium.

B=Number of cells that have crossed the wound line at the measurement time point for the negative baseline control sample (containing the cells and culture medium only).

C=Number of cells that have crossed the wound line at the measurement time point for the positive control containing the cells, culture medium, and the comparative growth factor stimulating agent sample used at the enabling concentration.

While this method provides an alternative to measurement of movement, the two methods are very similar and the preferred form of Cell Movement Bioassay incorporates the cell movement rather than cell number assessment.

B. Cell Proliferation Bioassay

The cell proliferation assay described in Example II should be used where the bioactive agent has been introduced at a final protein concentration of 0.01-10 mg protein/ml, more preferably 0.1 to 5 mg protein/ml, most preferably 1 mg protein/ml (as used in FIG. 6, where the best stimulating effect was seen at this concentration). In bioactive agent samples where the thymidine incorporation peak is seen at a dose lower than 1 mg protein/ml, then the protein concentration value yielding the highest thymidine incorporation value at or below 1 mg protein/ml should be used. In the case of bioactive agents where protein is not present, the value could be expressed in terms of "per mg of known chemical" (e.g., zine camosine) or "per mg total weight." (e.g., complex polysachharide mixture).

The thymidine incorporation values should be expressed as "counts per minute," although "decay per minute" may also be used, where appropriate. While the cell proliferation assay of the present invention uses thymidine incorporation as a marker to measure cell proliferation, some alternate marker of cell growth, such as absolute cell count using microscopy or an automated cell sorting apparatus, immunostaining using antibodies such as MIB1 staining, or dye incorporation using bromodeoxyuridine (BUDR) or a similar nuclear or other cellular organelle-incorporated dye may be employed.

In order to standardize this cell proliferation bioassay method, an enabling amount of comparative growth factor stimulating agent should be added to additional wells that contain the cells and culture medium but these wells do not receive any of the bioactive agent under assessment. While any of the comparative growth factor stimulating agents discussed above may be used, EGF1-53 is preferred.

An "enabling amount" of the comparative growth factor stimulating agent used in this Cell Proliferation Bioassay means a sufficient dosage to stimulate proliferation of the cells in the system by 50-100% of that maximally achievable using that particular comparative growth factor stimulating agent, more preferably 75-100%, most preferably 100%. The absolute concentration will therefore vary according to which comparative growth factor stimulating agent is to be used, and also the cell line to which it is to be applied. Such concentration determinations are well known in the art. In the case of EGF1-53 with HT-29 cells, this concentration happens to be 10 μg/ml. If a different growth factor or cell line is used, then a different concentration may be appropriate.

While the comparative growth factor stimulating agent should preferably be used in its fully active form, some forms of the comparative growth factor stimulating agents defined above are not fully active (e.g., EGF1-48), but still can be used for purposes of this invention.

The thymidine incorporation value should be measured for cell culture wells containing the comparative growth factor stimulating agent on the same assay day and under the same conditions as that applied to the cell culture wells containing the bioactive agent under assessment, and the negative baseline control containing any of the culture media discussed above, preferably DMEM. For example, taking the results summarized above in Example II, if wells in which EGF had been added caused a thymidine incorporation value of 300,000 CPM on Day 1 and 200,000 CPM on Day 2, using EGF as a standard comparator, then the same relative biological activity of colostrum is seen on both days with respect to what is seen for the EGF sample.

In the Example II test protocol discussed earlier, the marker for cell growth (i.e., thymidine) was added 24 hours after the bioactive agent had been introduced, and the subsequent collection of cells and measurement of thymidine incorporation into cells, performed 24 hours after addition of the marker. It is important to note, however, that the timing for adding the marker and performing the cell growth measurements is highly dependant upon the cell line used and the marker used for measuring growth. For example, when thymidine uptake is being used as the marker, then the thymidine can be added to the cell culture at a time point between when the bioactive agent is introduced up to 72 hours later (i.e. 0-72 hours), preferably 12-48 hours after the bioactive agent is introduced, most preferably 24 hours after the bioactive agent is introduced to the cell culture. Similarly, the timing of cell collection after the marker has been added is dependant on both the cell line used and the marker added. The timings of these additions and collections are well known in the art. For example, when thymidine uptake is being used as the marker, then the cell collection for thymidine uptake measurement may occur at any time 12-72 hours after its addition, preferably 12-48 hours after the marker is introduced, most preferably 24 hours after the marker has been introduced.

Whichever cell line and marker combination is chosen, one needs to wait a sufficient time between marker introduction and cell growth measurement to allow the marker to fairly reflect what is happening within the cells, and it is known within the prior art how to make these timing determinations for individual marker and cell line combinations. The two 24-hour time periods described in Example II represent the preferred timing points for the HT-29 cell lines in conjunction with a thymidine marker.

In some cases where alternative markers of cell growth are used for this Cell Proliferation Bioassay, the measurement time points discussed above may not be applicable. As noted above, one must wait for a sufficient time period to allow the marker to fairly reflect what is happening within the cells. For cell sorting or immunostaining methods, for example, the cells usually need to increase in number before the measurement may be made, so the measurement should not be made until 1-14 days after the test factors have been added to the wells, preferably 2-7 days after such bioactive agent test factors have been added. Persons familiar with these types of alternative marker systems for measuring cell growth will know how to choose an appropriate time point for making these measurements.

The final Proliferation Score may then be calculated using the following formula:

$$PS = \left(\frac{A-B}{C-B}\right) \times 10$$

where:

A=amount of CPM at the measurement time point for the wells containing the bioactive agent sample under assessment at the chosen concentration, along with the cells and culture medium.

B=amount of CPM at the measurement time point for the wells acting as the negative baseline control (containing the cells and culture medium only).

C=amount of CPM at the measurement time point for the wells acting as the positive comparator, containing the cells, culture medium, and the comparative growth factor stimulating agent sample used at the enabling concentration.

For purposes of this invention, the closer PS is to 10, the more ideal the bioactive agent is with respect to the pure comparative growth factor stimulating agent for purposes of enhancing cell proliferation, although the PS score for the bioactive agent may exceed that of the comparative growth factor stimulating agent to as much as 20.

While the description of this Cell Proliferation Bioassay has included a correction factor B for the baseline (negative) control, it is important to note that the scoring method may omit this factor in order to provide a simpler and quicker test that will not require the culturing of as many wells. In this case, the Proliferation Score would be calculated by the formula:

$$PS = \left(\frac{A}{C}\right) \times 10$$

where, as above:

A=amount of CPM at the measurement time point for the wells containing the bioactive agent sample under assessment at the chosen concentration, along with the cells and culture medium.

C=amount of CPM at the measurement time point for the wells acting as the positive comparator, containing the cells, culture medium and the comparative growth factor stimulating agent sample used at the enabling concentration.

While this method without inclusion of the baseline negative control may be simpler and quicker to perform, it will lose some of the precision incorporated into the $$PS = \left(\frac{A-B}{C-B}\right) \times 10$$

formula, because it does not correct for instability of the system. Therefore, the $$PS = \left(\frac{A-B}{C-B}\right) \times 10$$

formula is preferred for purposes of the Cell Proliferation Bioassay.

C. RPF Score

The "repair and protection factor" ("RPF") score for the bioactive agent may easily be calculated by the following formula:

*RPF Score=RS×PS* where:

RS=the cell restitution score; and

PS=the cell proliferation score for that bioactive agent. For purposes of the invention, the closer the RPF Score is to 100, the more ideal the bioactive agent is with respect to the pure comparative growth factor stimulating agent for purposes of enhancing cell migration and cell proliferation, although the RPF score for the bioactive agent may exceed that of the comparative growth factor stimulating agent to as much as 400. It is highly unlikely, however, that the RPF Score will exceed 300, especially if EGF1-53 is used as the comparative growth factor stimulating agent. In samples for bioactive agents where the test product only increased cell restitution or cell proliferation, but not both, then the absent RS or PS component should be accorded a value of 1 for the purposes of calculating the RPF Score.

While a bioactive agent may be scored separately for cell restitution and cell proliferation under this invention to enable direct comparisons of different samples of the same bioactive agent or samples of different bioactive agents for manufacturing quality control or marketing purposes, the single composite RPF Score may easily be calculated, and may be readily employed and understood for marketing purpose due to its simplicity.

The RPF Scoring method of the present invention is further illustrated by the following example:

EXAMPLE III

RPF Scoring Method

Figure 7:
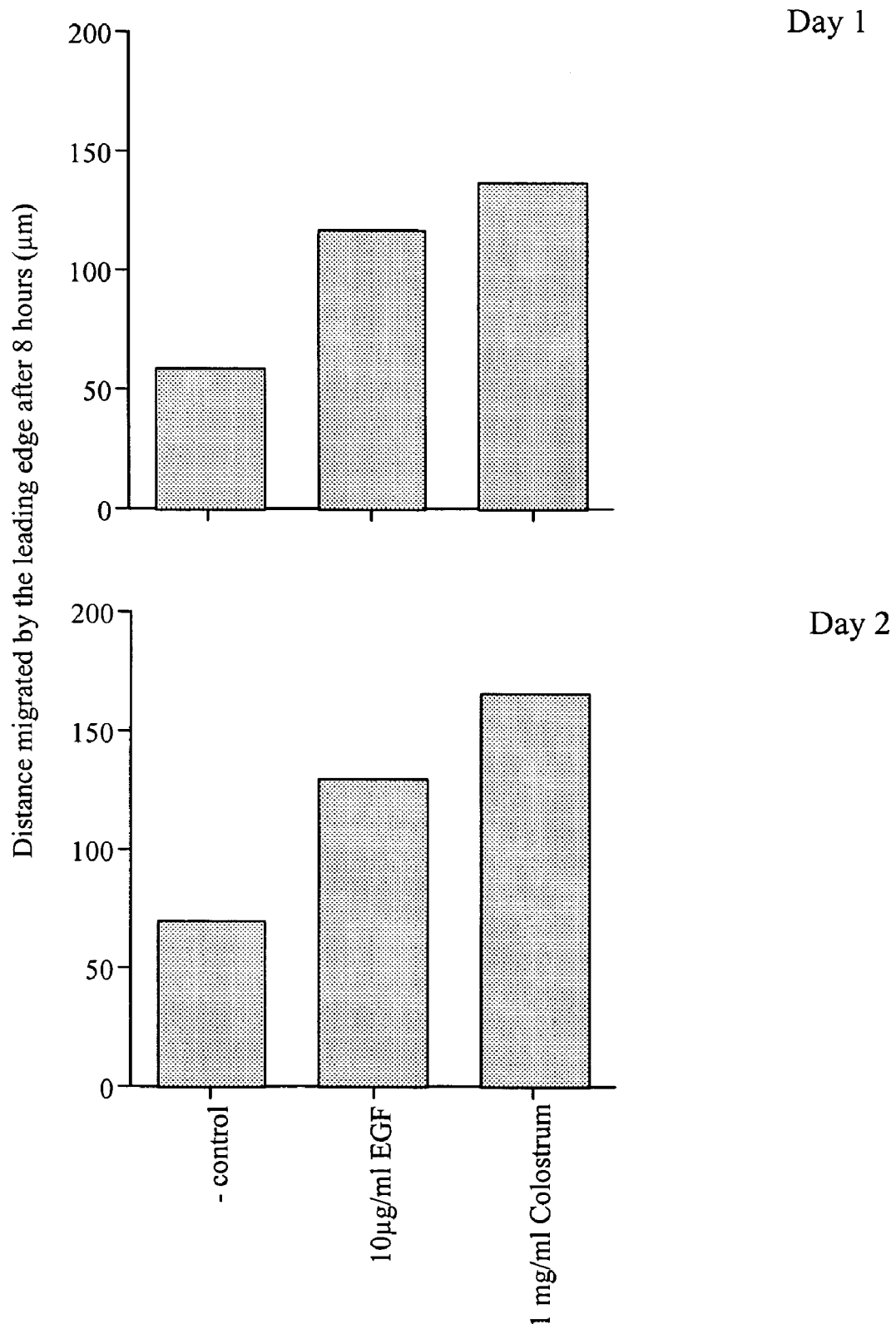
FIG. 7 is bar graphs comparing the effect of DMEM (negative control), EGF (positive control), and a colostrum sample on cell restitution at Day 1 vs. Day 2.

Commercial colostrum obtained from Sterling Technology of Brookings, South Dakota was used as the bioactive agent to be tested. The HT-29 human colonic cancer cell line obtained form the European Collection of Cell Cultures of the Health Protection Agency (Wiltshire, SP4 OJG,UK) was employed as the surrogate cell marker. Using the cell restitution bioassay method described above, the amount of cell migration produced by the same colostrum sample used at a final concentration of 1 mg protein/ml after eight hours of incubation was determined on two separate days (Day 1 vs. Day 2), as shown in FIG. 7. The absolute values of the respective distances of cell migration (µm) at 8 hours are shown in Table I as follows:

TABLE 1

|  | Control Sample | EGF Sample | Colostrum Sample |
|---|---|---|---|
| Day 1 | 59 | 117 | 137 |
| Day 2 | 70 | 130 | 166 |

As can be seen from Table 1, the absolute amount of movement in micrometers that the colostrum sample induced was different on the two days (137 µm for the study performed on Day 1 and 166 µm for the study performed on Day 2). However, the use of the restitution scoring system shows that the relative biological activity of the colostrum sample compared to the comparative growth factor (EGF) remains reasonably stable over these two assessment times. The respective Restitution Scores were calculated as follows:

$$RS_{Day1} = \left(\frac{137-59}{117-59}\right) \times 10 = 13.4$$

$$RS_{Day2} = \left(\frac{166-70}{130-70}\right) \times 10 = 16$$

These RS Scores show that the scoring method of the present invention should be useful for ensuring reproducibility results.

Figure 8:
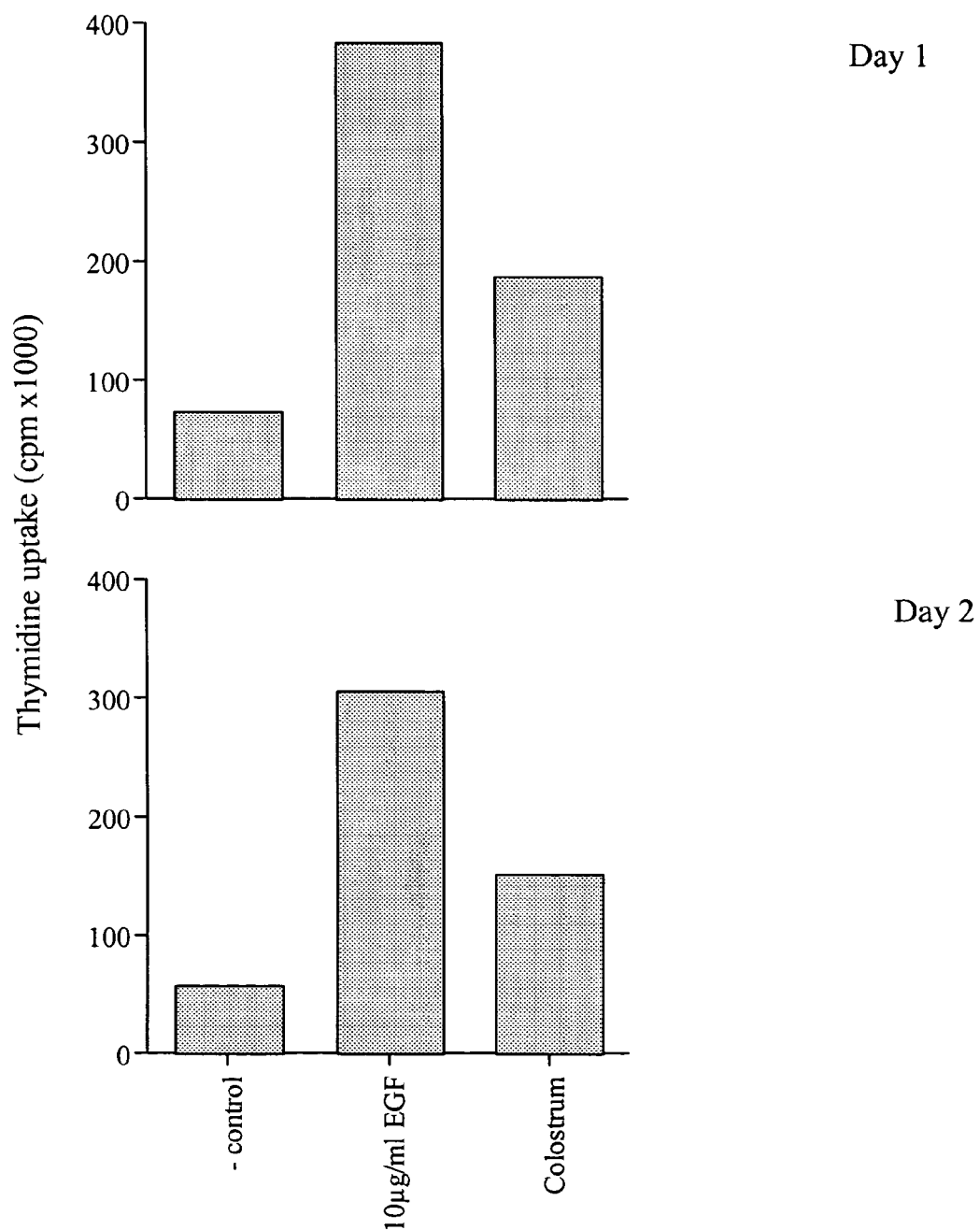
FIG. 8 is bar graphs comparing the effect of DMEM (negative control), EGF (positive control), and a colostrum sample on cell proliferation at Day 1 vs. Day 2.

Using the cell proliferation bioassay method described above, the amount of cell proliferation produced by the same colostrum sample, used at a final concentration of 1 mg protein/ml, was determined on two separate days (Day 1 vs. Day 2), as shown in FIG. 8. The absolute values of thymidine incorporation (CPM) induced by the colostrum sample on each of these two days are shown in Table 21 as follows:

TABLE 2

|  | Control Sample | EGF Sample | Colostrum Sample |
|---|---|---|---|
| Day 1 | 74,000 | 383,000 | 187,000 |
| Day 2 | 58,000 | 305,000 | 152,000 |

As can be seen from Table 2, the absolute CPM count that the colostrum sample induced was different on the two days (187,000 CPM for the study performed on Day 1 and 152,000 CPM for the study performed on day 2). However, use of the proliferation scoring system shows that the relative biological activity of the colostrum sample compared to the comparative growth factor (EGF) remains reasonably stable over these two assessment times. The respective Proliferation Scores were calculated as follows:

$$PS_{Day\ 1} = \left(\frac{187,000 - 74,000}{383,000 - 74,000}\right) \times 10 = 3.7$$

$$PS_{Day\ 2} = \left(\frac{152,000 - 58,000}{305,000 - 58,000}\right) \times 10 = 3.8$$

These PS scores show that this scoring method of the present invention should be useful for ensuring reproducible results.

Finally, the RPF Scores for the colostrum sample were calculated as follows:

RPF Score $_{Day\ 1}$=13.4×3.7=49.58

RPF Score $_{Day\ 2}$=16×3.8=60.80

Again, these RPF Score results are relatively consistent, and provide a ready means for comparing the colostrum sample against EGF used as the comparative growth factor stimulating agent ideal for purposes of enhancing cell migration and cell proliferation.

Much of the foregoing discussion has been directed to epithelial cells like HT-29, but the novel scoring methods of this invention my be applied to all functional cells, as defined above, which includes the inflammatory process. In the case of testing bioactive agents that influence this inflammatory process, one should use white blood cells, such as lymphocytes, macrophages, and/or dendritic cells.

Cell Movement Bioassays will not generally be relevant for testing bioactive agents that influence this inflammatory response function. Therefore, only the Cell Proliferation Bioassay need be used. The comparative growth factor stimulating agent used in the positive control should be a molecule that influences proliferation of those cells, such as members of the cytokine family. Interleukin 8 and tumor necrosis factor alpha are examples. As described earlier, the marker used can be thymidine, or may be some alternate marker of cell growth, such as absolute cell count using microscopy or an automated cell sorting apparatus, immunostaining using antibodies such as MIB1 staining, or dye incorporation using bromodeoxyuridine (BUDR), or a similar nuclear or other cellular organelle-incorporated dye may be employed.

For bioactive agents that stimulate or enhance proliferation in these inflammatory cells, one should use the same formula:

$$PS = \left(\frac{A - B}{C - B}\right) \times 10$$

with A, B, and C being defined as above. This test method could also be called an "Immune Enhancement Score" ("IES").

Certain bioactive agents, however, act to dampen the immune response. Colostrum used to treat the effects of irritable bowel syndrome ("IBS") is an example of such an application. In the case of factors which have immune dampening effects, positive biological activity takes the form of the bioactive agent being able to dampen down an immune response, demonstrated by reducing the amount of cell proliferation of immune cells that have been stimulated to proliferate (activated). The method by which this is tested is to take a set of immune cells and then stimulate their growth by adding an "immune cell proliferation enhancing factor." The form that this immune cell proliferation enhancing factor takes may be by adding a second set of immune cells from a second individual (causing the two sets of cells to fight against each other), or alternatively, by adding a single cytokine protein or peptide (such as tumor necrosis factor alpha), or a collection of cytokines, in order to make the first set of immune cells proliferate. The concentration of cytokines to be added or the number of second set of immune cells to be added in order to stimulate the immune cells, causing activation, are well known in the art.

Figure 9:
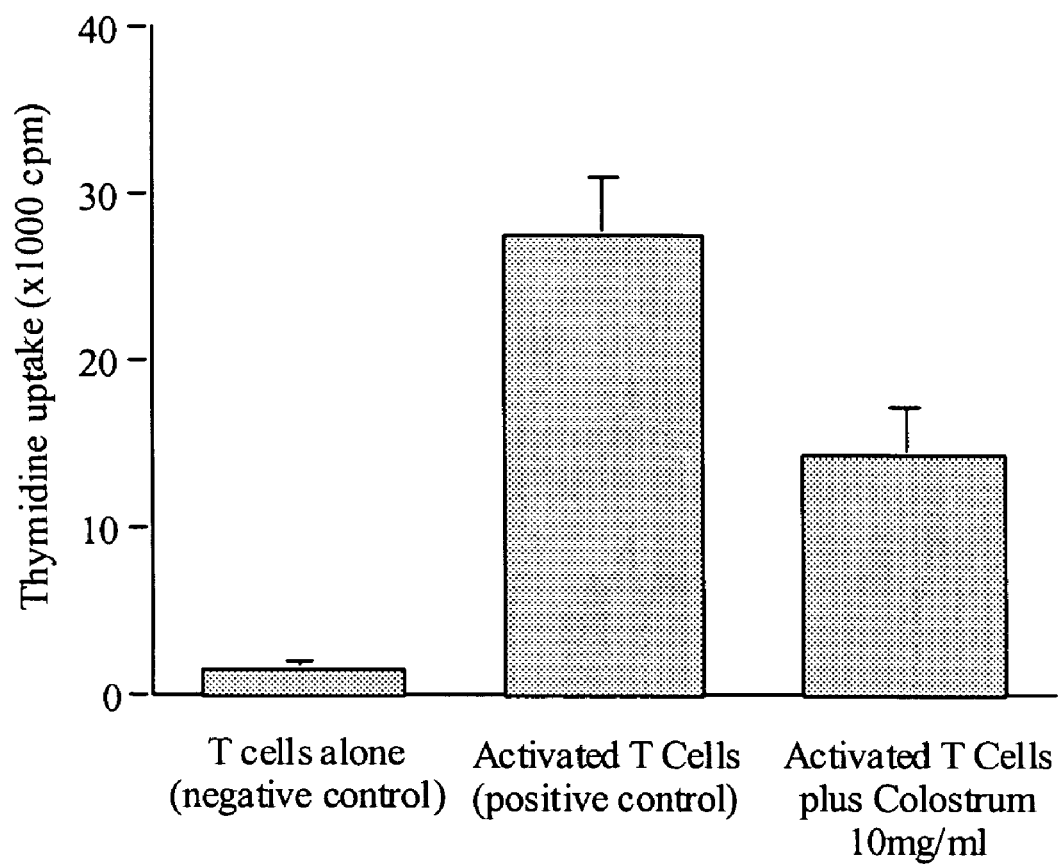
FIG. 9 is a bar graph showing the relative levels of cell proliferation (thymidine uptake) for T cells, T cells/dendritic cells mixtures, and a colostrum solution applied to the T cells/dendritic cells mixture.

The bioactive agent under test is then added to these activated immune cells. Any immune dampening will be shown by its ability to reduce proliferation of these activated immune cells. FIG. 9 illustrates an "Immune Suppression System" that compares the thymidine uptake values for cultures containing: T cells alone (i.e., baseline negative control) at 1,000 cpm; a mixture of T cells and dendritic cells (i.e., activated immune cells with the dendritic cells acting as the "immune cell proliferation enhancing factor") at 29,000 cpm; and a 10% colostrum solution applied to the T cells/dendritic cells mixture at 15,000 cpm. Pending application U.S. Ser. No. 10/892939 filed on Jul. 16, 2004 by the inventor of this application describes this experiment in greater detail, and is hereby incorporated by reference.

The Immune Suppression Score ("ISS") for such a bioactive agent that dampens an immune response should be calculated by the following formula:

$$ISS = \left(\frac{C - A}{C - B}\right) \times 10$$

where:

A=amount of cpm at the measurement time point for wells containing the bioactive agent sample at the chosen concentration incubated with the immune cells and the immune cell proliferation enhancing factor at the chosen concentration.

B=amount of cpm at the measurement time point for the wells containing the immune cells incubated in the growth media alone (negative baseline control).

C=amount of cpm at the measurement time point for wells containing the immune cells and the immune cell proliferation enhancing factor at the chosen concentration.

Using the thymidine uptake values disclosed above, the ISS for colostrum would be:

$$ISS = \left(\frac{29{,}000 - 15{,}000}{29{,}000 - 1{,}000}\right) \times 10 = 5.$$

The above specification, examples, and data provide a complete description of the invention relating to the method for scoring the capacity of a bioactive agent to enhance cell migration and/or cell proliferation. Since many embodiments of the invention can be made without departing from the spirit and scope of the invention, the invention resides in the claims hereinafter appended.

What is claimed is:

1. A method for scoring a bioactive agent's capacity to promote migration and proliferation of mammalian cells to contribute to healing of an injury to functional tissue of the mammalian cells, or maintenance of the mammalian cells grown in laboratory cell cultures, comprising:

(a) Selecting a functional tissue mammalian cell line;

(b) Conducting a cell migration bioassay test on the functional tissue mammalian cell line comprising growing out a first cell culture of the functional tissue mammalian cell line to create a first monolayer; wounding the first monolayer to create a first gap denuded of functional mammalian tissue cells having a first anterior edge; incubating the first cell culture of the functional tissue mammalian cell line with between 0.01 mg protein/ml and 10 mg protein/ml of a bioactive agent; and measuring at an appropriate time point after the wound to the first monolayer was created a distance traveled by the first anterior edge of a denuded first gap in the first cell culture of the functional tissue mammalian cell line compared with the first anterior edge's initial position when the wound to the first monolayer was created;

(c) Conducting a cell proliferation bioassay test on the functional tissue mammalian cell line comprising growing out a second cell culture of the functional tissue mammalian cell line; incubating the second cell culture of the functional tissue mammalian cell line with between 0.01 mg protein/mi and 10 mg protein/ml of the bioactive agent; adding to the incubated cell culture at an appropriate time point after the addition of the bioactive agent a first cell growth marker; within an appropriate time point after the first cell growth marker was added to the incubated cell culture, locating the first cell growth marker to measure the degree of cell growth within the second cell culture of the functional tissue mammalian cell line;

(d) forming a positive control cell culture by growing out a third cell culture of the functional tissue mammalian cell line to create a second monolayer, wounding the second monolayer to create a second gap denuded of functional mammalian tissue cells having a second anterior edge, incubating the third cell culture of the functional tissue mammalian cell line with an enabling amount of comparative growth factor stimulating agent, and measuring at an appropriate time point after the second wound was created a distance traveled by the second anterior edge of a second denuded gap in the third cell culture of the functional tissue mammalian cell line compared with the second anterior edge's initial position when the second wound was created; and growing out a fourth cell culture of the functional tissue mammalian cell line, incubating the fourth cell culture of the functional tissue mammalian cell line with the enabling amount of comparative growth factor stimulating agent, adding to the incubated cell culture of the fourth cell culture at an appropriate time point after the addition of the comparative growth factor stimulating agent to the fourth cell culture a second cell growth marker, within an appropriate time point after the second cell growth marker was added to the incubated cell culture of the fourth cell culture, locating the second cell growth marker to measure a degree of cell growth within the fourth cell culture of the functional tissue mammalian cell line;

(e) forming a negative baseline control cell culture by growing out a fifth cell culture of the functional tissue mammalian cell line to create a third monolayer, wounding the third monolayer to create a third gap denuded of functional mammalian tissue cells having a third anterior edge, incubating the fifth cell culture of the functional tissue mammalian cell line without the comparative growth factor stimulating agent and the bioactive agent, and measuring at an appropriate time point after the third wound was created a distance traveled by the third anterior edge of a third denuded gap in the fifth cell culture of the functional tissue mammalian cell line compared with the third anterior edge's initial position when the third wound was created; and growing out a sixth cell culture of the functional tissue mammalian cell line, incubating the sixth cell culture of the functional tissue mammalian cell line without the comparative growth factor stimulating agent and the bioactive agent, adding to the incubated cell culture of the sixth cell culture a third cell growth marker, within an appropriate time point after the third cell growth marker was added to the incubated cell culture of the sixth cell culture, locating the third cell growth marker to measure a degree of cell growth within the sixth cell culture of the functional tissue mammalian cell;

(f) Calculating a cell restitution score (RS) for the bioactive agent by means of the formula:

$$RS = \left(\frac{A}{C}\right) \times 10$$

where:

A=the amount of movement of the anterior edge of the functional tissue mammalian cells of the first cell culture at a measurement time point for the bioactive agent at a chosen concentration;

B=the amount of movement of the anterior edge of the functional tissue mammalian cells of the fifth cell culture at the measurement time point for the negative baseline control cell culture; and C=the amount of movement of the anterior edge of functional tissue mammalian cells of the third cell culture at the measurement time point for the positive control cell culture;

(g) Calculating a cell proliferation score (PS) for the bioactive agent by means of the formula:

$$RS = \left(\frac{A-B}{C-B}\right) \times 10$$

where:
- A=the degree of cell growth exhibited at the measurement time point by the first cell growth marker;
- B=the degree of cell growth exhibited at the measurement time point by the third growth cell marker for the negative baseline control cell culture; and
- C=the degree of cell growth exhibited at the measurement time point by the second cell growth marker for the positive control cell culture; and (h) Calculating a composite cell repair and protection factor (RPF) score for the bioactive agent by means of the formula:

$$RPF = RS \times PS.$$

2. The method according to claim 1, wherein the bioactive agent is colostrum.

3. The method according to claim 2 wherein the bioactive agent is bovine colostrum.

4. The method according to claim 1, wherein the bioactive agent is hSP.

5. The method according to claim 1, wherein the bioactive agent is zinc-carnosine.

6. The method according to claim 1, wherein the injury to the functional tissue cells is caused by a peptic ulcer in the mammal.

7. The method according claim 1, wherein the injury to the functional tissue cells is caused by a gastric ulcer in the mammal.

8. The method according to claim 1, wherein the injury to the functional tissue cells is caused by inflammatory bowel disease in the mammal.

9. The method according to claim 1, wherein the mammal is experiencing irritable bowel syndrome.

10. The method according to claim 1, wherein the wounding is caused by non-steroidal or steroidal anti-inflammatory drugs.

11. The method according to claim 1, wherein the injury to the functional tissue cells is caused by a bacteria-based infectious agent.

12. The method according to claim 1, wherein the injury to the functional tissue cells is caused by systemic lupus, erythematosis, or rheumatoid arthritis.

13. The method according to claim 1, wherein the injury to the functional tissue cells is caused by a surface cut to the skin of the mammal.

14. The method according to claim 1, wherein the injury to the functional tissue cells is caused by an abrasion to the cornea of the eye of the mammal.

15. The method according to claim 1, wherein the injury to the functional tissue cells is caused by a burn or corrosive agent.

16. The method according to claim 1, wherein the functional tissue mammalian cell line is selected from a group consisting of human colonic cancer cell lines HT-29 and caco2 cells, the HIE human intestinal line, the rat intestinal cell line RIE6, the gastric cell line AGS, IEC-6 cell lines, IEC-17 cell lines, T84 cell lines, NRK cell lines, and inflammatory cells of primary origin or long-term culture cell lines.

17. The method according to claim 16, wherein the primary origin or long-term culture inflammatory cells are neutrophils, lymphocytes, macrophages, or dendritic cells.

18. The method according to claim 1, wherein the comparative growth factor stimulating agent is epidermal growth factor.

19. The method according to claim 1, wherein a growth media used in the negative-baseline control cell culture is Dulbecco/Vogt modified Eagle's minimal essential medium.

20. The method according to claim 1, wherein the first cell culture and the second cell culture are incubated by the bioactive agent at 1 mg protein/ml.

21. The method according to claim 1, wherein the time point for measuring the distance traveled by the first anterior edge, the second anterior edge, and third anterior edge of the first denuded gap, second denuded gap, and third denuded gap is 4-24 hours after the wound to the first monolayer, the second monolayer, and third monolayer was created.

22. The method according to claim 21, wherein the time point for measuring the distance traveled by the first anterior edge, the second anterior edge, and third anterior edge of the first denuded gap, second denuded and third denuded gap is 8 hours after the wound to the first monolayer, the second monolayer, and third monolayer was created.

23. The method according to claim 1, wherein the first, second, and third markers comprise cell growth thymidine incorporation using [$^3$H]-thymidine.

24. The method according to claim 1, wherein the first, second, and third cell growth markers comprise absolute cell count.

25. The method according to claim 1, wherein the first, second, and third cell growth markers comprise immunostaining.

26. The method according to claim 1, wherein the first, second, and third cell growth markers comprise dye incorporation.

27. The method according to claim 1, wherein the time point for adding the first cell growth marker is 0-48 hours after the incubation of the bioactive agent.

28. The method according to claim 1, wherein the time point for locating the first cell growth marker, the second cell growth mark, and the third cell growth marker to measure the degree of cell growth is 12-72 hours after the first cell growth marker, the second cell growth mark, and the third cell growth marker were added.

29. The method according to claim 1, wherein the time point for locating the first cell growth marker, the second cell growth mark, and the third cell growth marker to measure the degree of cell growth is 24 hours after the first cell growth marker, the second cell growth mark, and the third cell growth marker were added.

* * * * *